United States Patent
Nayak

(10) Patent No.: US 9,320,704 B1
(45) Date of Patent: Apr. 26, 2016

(54) TOPICAL FACIAL MASK COMPOSITION FOR SKIN CARE

(71) Applicant: Archana Nayak, Stockton, CA (US)

(72) Inventor: Archana Nayak, Stockton, CA (US)

( * ) Notice: Subject to any disclaimer, the term of this patent is extended or adjusted under 35 U.S.C. 154(b) by 0 days.

(21) Appl. No.: 14/503,579

(22) Filed: Oct. 1, 2014

(51) Int. Cl.
| | | |
|---|---|---|
| *A61K 8/97* | (2006.01) | |
| *A61K 8/25* | (2006.01) | |
| *A61K 8/02* | (2006.01) | |
| *A61Q 19/10* | (2006.01) | |
| *A61Q 19/08* | (2006.01) | |

(52) U.S. Cl.
CPC .................. *A61K 8/97* (2013.01); *A61K 8/0212* (2013.01); *A61K 8/25* (2013.01); *A61Q 19/08* (2013.01); *A61Q 19/10* (2013.01); *A61K 2800/59* (2013.01)

(58) Field of Classification Search
None
See application file for complete search history.

(56) References Cited

PUBLICATIONS

Elise's recipe "Red lentil dal," posted online Sep. 8, 2011; http://www.simplyrecipes.com/recipes/red_lentil_dal/.*

Ishanigam's blog article entitled "Reduce facial hair and whiten skin with ancient DIY indian ubtan," available online Apr. 22, 2012; https://ishanigam.wordpress.com/2012/04/22/reduce-facial-hair-and-whiten-skin-with-ancient-diy-indian-ubtan/.*

"Lentils, dry, all" online conversion accessed Feb. 12, 2015; http://www.cookitsimply.com/measurements/cups/lentils-dry-all-0070-014i0.html.*

Tanzystylefile's blog article entitled "Reivew—Forest Essential Multani Mitti Ubtan," available online Nov. 23, 2011; http://tanzystylefile.blogspot.com/2011/11/review-forest-essential-multani-mitti.html.*

Oshin's blog article entitled "My homemade ubtan recipe for skin brightening," available on line Feb. 17, 2014; http://www.makeupandbeautyhome.com/2014/02/my-homemade-ubtan-recipe-for-skin-brightening.html.*

Shivi "Red lentils (masoor dal) body scrub & face pack for oily/dry skin: do it yourself," posted online Aug. 13, 2013; http://www.cosmochics.com/red-lentils-masoor-dal-body-scrub-face-pack-for-oilydry-skin-do-it-yourself/.*

\* cited by examiner

*Primary Examiner* — David J Blanchard
*Assistant Examiner* — Alissa Prosser

(57) ABSTRACT

In certain embodiments, the invention is directed to a formulation for providing skin tightening which includes two or more of the following agents: red split lentils, Multani Mitti, charoli, chandan powder, and turmeric powder. Two or more of the agents can be ground and combined together in an effective amount. The combined agents can be additionally combined with a topical excipient.

5 Claims, No Drawings

TOPICAL FACIAL MASK COMPOSITION FOR SKIN CARE

TECHNICAL FIELD

The present disclosure relates generally to skin care and more specifically to a topical facial mask composition for skin care.

BACKGROUND

Throughout history, people have struggled to keep their face looking young, clean and vibrant. Various types of facial masks have been used to remove oils, cleanse pores, moisturize or brighten skin tone to improve the beauty of skin in various cultures.

Topical facial masks are ordinarily applied to the face in a thin layer. After a period of wearing the facial mask, in which the duration varies, the masks are removed by using water, a damp cloth or by peeling the solidified mask off.

Purposes for using topical facial masks differ. Some facial masks improve general skin health by cleansing, brightening, solidifying, drying or moisturizing the face. Other facial masks improve specific skin issues such as acne scars or hyper-pigmentation. The type of facial mask used will depend not only on the purpose of the facial mask, but also the skin type. What is needed is a facial mask to address the deficiencies of the present types of facial masks.

DETAILED DESCRIPTION

This present disclosure involves a combination of materials described below for a facial mask for cleansing, tightening, and brightening a person's skin tone. The present disclosure also involves a method for the application of the combination of materials for the facial mask.

In an embodiment, the composition results from the processing of a combination of red split lentils, Fuller's earth, charoli, sandalwood powder along with milk, yogurt or rose water. Depending on the availability and the needs of the user, turmeric powder may be added.

In an embodiment, the dry red split lentils and charoli can be coarsely ground or granulated. The composition can comprise a proportion of approximately 1 cup of coarsely ground or granulated dry red split lentils and one tablespoon of coarsely ground charoli. As used herein, the term "coarsely ground" can mean that the particles are ground into grains or small particles. Charoli, (also known as chironji) is a seed from a Buchanania lanzan tree. In an embodiment, the proportional amount of charoli relative to the amount of dry red split lentils can vary depend on the person's skin type. For example, if the person's skin type is normal to oily, the composition can include approximately 1 tablespoon of coarsely ground charoli and one cup of coarsely ground dry red split lentils. If the skin type is normal to dry, the composition can include approximately 1.5 tablespoons of coarsely ground charoli and one cup of coarsely ground dry red split lentils.

In an embodiment, the dry red split lentils and charoli can be finely ground or granulated to form a more powdery substance.

Multani Mitti, also known as Fuller's earth, is a clay material that has the ability to adsorb impurities. In an embodiment, the composition can include approximately ¾ cup of finely ground Multani Mitti. As used herein, the term "finely ground" means that the particles are ground or pulverized into relatively small pieces or a powder.

Chandan powder, also known as sandalwood powder, is a powder that derives from woods from trees in the genus Santalum. In an embodiment, the composition can include approximately 1 tablespoon of finely ground chandan powder.

Turmeric is an herbaceous plant of the ginger family. The turmeric rhizome, while in a raw and dried state, can be finely ground into a powder. In an embodiment, the composition can include approximately 1 tablespoon of finely ground turmeric powder.

In an embodiment, the composition, including the coarsely ground dry red split lentils, the coarsely ground charoli, the finely ground Multani Mitti, the finely ground chandan powder, and the finely ground turmeric powder, can be mixed into a homogenous blend. In an embodiment, the blend can be placed into an air tight container. In an embodiment, the blend can be stored in a container and placed in a dark, cool location such as a refrigerator.

In an embodiment, the composition can further include a pharmaceutically acceptable topical excipient in the form of a gel, cream, ointment, foam, solution or suspension.

In an embodiment, when the topical facial mask is ready for use, 2 tablespoons of the blend can be mixed with 2-3 tablespoons of a liquid such as milk, liquefied yogurt or rose water. In an embodiment, if the person has normal to oily skin, the blend can be mixed with rose water, but not with milk or liquefied yogurt. In an embodiment, if the person has normal to dry skin, the blend can be mixed with milk or yogurt, but not with rose water.

In an embodiment, after the blend is mixed with the liquid, the new mixture can be set aside for approximately 20-30 minutes to form a paste-like consistency. Then, the new mixture can be applied to the person's face in order to create a 1-2 mm layer.

In an embodiment, this layer can remain on the person's face overnight. In another embodiment, the layer can remain on the person's face for approximately 30-45 minutes. After the prescribed time has finished, the layer can be removed by washing or rinsing it off with water. In an embodiment, cold water can be used to wash off or rinse off the layer, but if this is not tolerable to the person, lukewarm water is acceptable. In an embodiment, the use of hot water to rinse and remove the layer can be avoided because the hot water can cook the lentils in the paste/mixture that is applied to the face. This can shrink the paste/mixture which in turn can shrink the skin which should be avoided.

The present disclosure is not to be limited in scope by the specific embodiments disclosed in the examples which are intended as illustrations of a few aspects of the invention and any embodiments that are functionally equivalent are within the scope of this invention. Indeed, various modifications of the disclosure in addition to those shown and described herein will become apparent to those skilled in the art and are intended to fall within the scope of the appended claims.

What is claimed is:

1. A method of skin tightening comprising:
applying a composition comprising a homogenous blend comprising red split lentils, Multani Mitti, charoli, chandan powder, and turmeric powder to the skin of a person's face, wherein the composition comprises a proportion of approximately 1 cup of the red split lentils, approximately 1 tablespoon of the charoli, approximately 0.75 cups of the Multani Mitti, approximately 1 tablespoon of the chandan powder, and approximately 1 tablespoon of the turmeric powder, the blend ground and in an effective amount to provide skin tightening, the composition further comprising at least one liquid selected from the group consisting of rose water, water, milk, and liquefied yogurt, and wherein the composition is in a form of a gel, cream, paste, ointment, foam, solution or suspension; and removing the composition from the person's face using cold or lukewarm water.

2. The method of claim 1, wherein the applying the composition is for a time period between 30 and 45 minutes.

3. The method of claim 1, wherein the red split lentils and charoli are coarsely ground and the Multani Mitti and chandan powder are finely ground.

4. The method of claim 1, comprising approximately 2 tablespoons of the composition mixed with at least one liquid selected from the group consisting of approximately 2 tablespoons of rose water, approximately 2 tablespoons of water, approximately 2 tablespoons of milk, and approximately 2 tablespoons of-liquefied yogurt.

5. The method of claim 1, wherein the composition is applied to the person's face in a layer having a thickness between 1 mm and 2 mm.

* * * * *